US005721133A

United States Patent [19]
Dasmahapatra

[11] Patent Number: 5,721,133
[45] Date of Patent: Feb. 24, 1998

[54] PROTEASE ASSAYS

[75] Inventor: Bimalendu Dasmahapatra, Nutley, N.J.

[73] Assignee: Schering Corporation, Kenilworth, N.J.

[21] Appl. No.: 456,582

[22] Filed: Jun. 1, 1995

Related U.S. Application Data

[62] Division of Ser. No. 333,901, Nov. 3, 1994, Pat. No. 5,599,906, which is a continuation of Ser. No. 923,988, filed as PCT/US91/02283, Apr. 10, 1991, which is a continuation-in-part of Ser. No. 509,007, Apr. 13, 1990, abandoned.

[51] Int. Cl.$^6$ ................................ C12N 1/21; C12Q 1/37
[52] U.S. Cl. .................... 435/252.3; 435/23; 536/23.4
[58] Field of Search ........................ 424/9, 2; 435/5, 435/6, 23, 29, 172.1, 172.3, 212, 240.1, 254.11, 252.3, 255.1, 320.1, 69.1, 219; 530/350; 536/23.2, 23.4

[56] References Cited

U.S. PATENT DOCUMENTS

| | | | |
|---|---|---|---|
| 4,617,149 | 10/1986 | DiMarchi et al. | 530/324 |
| 4,740,461 | 4/1988 | Kaufman | 435/69.1 |
| 4,743,679 | 5/1988 | Cohen et al. | 530/350 |
| 4,769,326 | 9/1988 | Rutter | 435/68.1 |
| 4,833,080 | 5/1989 | Brent et al. | 435/172.3 |
| 4,981,784 | 1/1991 | Evans et al. | 435/6 |

FOREIGN PATENT DOCUMENTS

WO 90/06369  6/1990  WIPO.

OTHER PUBLICATIONS

Roberts, et al., *Science*, 248, 358–361 (1990).
Craig, et al., *Antiviral Res.*, 16, 295–305 (1991).
Metzler, D.E., in *Biochemistry. The Chemical Reactions of Living Cells*, Academic Press, New York, p. 321 (1977).
Choo, et al., *DNA*, 5, 529 (1986).
Farmerie, et al., *Science*, 236, 305 (1987).
Giniger, et al., *Cell*, 40, 767 (1985).
Giniger, et al., *Nature*, 330, 670 (1987).
Guarente, et al., *Proc. Nat. Acad. Sci. USA*, 79, 7410 (1982).
Hanecak, et al., *Cell*, 37, 1063 (1984).
Ito, et al., *J. Bacteriol.*, 153, 163 (1983).
Johnson, et al., *Proc. Nat. Acad. Sci. USA*, 76, 5061 (1979).
Johnston, et al., *Proc. Nat. Acad. Sci. USA*, 79, 6971 (1982).
Johnston, et al., *Mol. Cell. Biol.*, 4, 1440 (1984).
Johnston, et al., *Proc. Nat. Acad. Sci. USA*, 83, 6353 (1986).
Kakidani, et al., *Cell*, 52, 161 (1988).
Miller, et al., *Arch. Biochem. Biophys.*, 139, 104 (1970).
Okayama, et al., *Mol. Cell. Biol.*, 3, 280 (1983).
Pfarr, et al., *DNA*, 4, 461 (1985).
Ptashne, *Nature*, 335, 683 (1988).
Rothstein, *Meth. Enzymol.*, 101, 202, (1983).
Ratner, et al., *Nature*, 313, 277 (1985).
Sauer, *Nature*, 276, 301 (1978).
Toyoda, et al., *Cell*, 45, 761 (1986).
Webster, et al., *Cell*, 52, 169 (1988).
Ma, et al., *Gene*, 58, 201 (1987).
Ma, et al., *Cell*, 48, 847 (1987).
Meek, et al., *Proc. Nat. Acad. Sci. USA*, 86, 1841 (1989).
Roberts et al. (1981) Nature 290: 422–424 "Two Mutations that Alter the Regulatory Activity of *E. coli* RecA Protein".
Paulmier et al. (1987) EMBO J. 6: 3539–3542, "gal4 Transcription Activator Protein of Yeast can Function as a Repressor in *Escherichia coli*".

*Primary Examiner*—Robert A. Wax
*Assistant Examiner*—Daniel Mytelka
*Attorney, Agent, or Firm*—Norman C. Dulak

[57] ABSTRACT

Hybrid regulatory proteins are provided which contain amino acid sequences that are susceptible to cleavage by specific proteolytic enzymes. When acted upon by such enzymes, the hybrid regulatory proteins are rendered substantially less active, thereby altering the rate of production of products of indicator genes that are controlled by the regulatory proteins. Also provided are DNAs encoding such regulatory proteins, recombinant vectors and transformed eukaryotic cells containing such DNAs, and methods for identifying inhibitors of the specific proteolytic enzymes.

25 Claims, 1 Drawing Sheet

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
( A ) LENGTH: 881 amino acids
( B ) TYPE: amino acid
( D ) TOPOLOGY: linear ( i i ) MOLECULE TYPE: peptide ( x i ) SEQUENCE DESCRIPTION: SEQ ID NO: 1:

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
                20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
    50                  55                      60

Glu Gln Leu Phe Leu Leu Ile Phe Pro Arg Glu Asp Leu Asp Met Ile
65                      70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
            115                 120                 125

Ala Thr Ser Ser Ser Glu Glu Ser Ser Asn Lys Gly Gln Arg Gln Leu
    130                 135                 140

Thr Val Ser Ile Asp Ser Ala Ala His His Asp Asn Ser Thr Ile Pro
145                 150                 155                 160

Leu Asp Phe Met Pro Arg Asp Ala Leu His Gly Phe Asp Trp Ser Glu
                165                 170                 175

Glu Asp Asp Met Ser Asp Gly Leu Pro Phe Leu Lys Thr Asp Pro Asn
            180                 185                 190

Asn Asn Gly Phe Phe Gly Asp Gly Ser Leu Leu Cys Ile Leu Arg Ser
        195                 200                 205

Ile Gly Phe Lys Pro Glu Asn Tyr Thr Asn Ser Asn Val Asn Arg Leu
    210                 215                 220

Pro Thr Met Ile Thr Asp Arg Tyr Thr Leu Ala Ser Arg Ser Thr Thr
225                 230                 235                 240

Ser Arg Leu Leu Gln Ser Tyr Leu Asn Asn Phe His Pro Tyr Cys Pro
                245                 250                 255

Ile Val His Ser Pro Thr Leu Met Met Leu Tyr Asn Asn Gln Ile Glu
            260                 265                 270
```

-continued

```
Ile Ala Ser Lys Asp Gln Trp Gln Ile Leu Phe Asn Cys Ile Leu Ala
        275                 280                 285

Ile Gly Ala Trp Cys Ile Glu Gly Glu Ser Thr Asp Ile Asp Val Phe
        290                 295                 300

Tyr Tyr Gln Asn Ala Lys Ser His Leu Thr Ser Lys Val Phe Glu Ser
305                     310                 315                 320

Gly Ser Ile Ile Leu Val Thr Ala Leu His Leu Leu Ser Arg Tyr Thr
                325                 330                 335

Gln Trp Arg Gln Lys Thr Asn Thr Ser Tyr Asn Phe His Ser Phe Ser
        340                 345                 350

Ile Arg Met Ala Ile Ser Leu Gly Leu Asn Arg Asp Leu Pro Ser Ser
        355                 360                 365

Phe Ser Asp Ser Ser Ile Leu Glu Gln Arg Arg Arg Ile Trp Trp Ser
        370                 375                 380

Val Tyr Ser Trp Glu Ile Gln Leu Ser Leu Leu Tyr Gly Arg Ser Ile
385                     390                 395                 400

Gln Leu Ser Gln Asn Thr Ile Ser Phe Pro Ser Ser Val Asp Asp Val
                405                 410                 415

Gln Arg Thr Thr Thr Gly Pro Thr Ile Tyr His Gly Ile Ile Glu Thr
                420                 425                 430

Ala Arg Leu Leu Gln Val Phe Thr Lys Ile Tyr Glu Leu Asp Lys Thr
        435                 440                 445

Val Thr Ala Glu Lys Ser Pro Ile Cys Ala Lys Lys Cys Leu Met Ile
    450                 455                 460

Cys Asn Glu Ile Glu Glu Val Ser Arg Gln Ala Pro Lys Phe Leu Gln
465                 470                 475                 480

Met Asp Ile Ser Thr Thr Ala Leu Thr Asn Leu Leu Lys Glu His Pro
                485                 490                 495

Trp Leu Ser Phe Thr Arg Phe Glu Leu Lys Trp Lys Gln Leu Ser Leu
            500                 505                 510

Ile Ile Tyr Val Leu Arg Asp Phe Phe Thr Asn Phe Thr Gln Lys Lys
            515                 520                 525

Ser Gln Leu Glu Gln Asp Gln Asn Asp His Gln Ser Tyr Glu Val Lys
    530                 535                 540

Arg Cys Ser Ile Met Leu Ser Asp Ala Ala Gln Arg Thr Val Met Ser
545                 550                 555                 560

Val Ser Ser Tyr Met Asp Asn His Asn Val Thr Pro Tyr Phe Ala Trp
                565                 570                 575

Asn Cys Ser Tyr Tyr Leu Phe Asn Ala Val Leu Val Pro Ile Lys Thr
            580                 585                 590

Leu Leu Ser Asn Ser Lys Ser Asn Ala Glu Asn Asn Glu Thr Ala Gln
            595                 600                 605

Leu Leu Gln Gln Ile Asn Thr Val Leu Met Leu Leu Lys Lys Leu Ala
    610                 615                 620

Thr Phe Lys Ile Gln Thr Cys Glu Lys Tyr Ile Gln Val Leu Glu Glu
625                 630                 635                 640

Val Cys Ala Pro Phe Leu Leu Ser Gln Cys Ala Ile Pro Leu Pro His
                645                 650                 655

Ile Ser Tyr Asn Asn Ser Asn Gly Ser Ala Ile Lys Asn Ile Val Gly
            660                 665                 670

Ser Ala Thr Ile Ala Gln Tyr Pro Thr Leu Pro Glu Glu Asn Val Asn
        675                 680                 685

Asn Ile Ser Val Lys Tyr Val Ser Pro Gly Ser Val Gly Pro Ser Pro
690                 695                 700
```

```
Val  Pro  Leu  Lys  Ser  Gly  Ala  Ser  Phe  Ser  Asp  Leu  Val  Lys  Leu  Leu
705            710                      715                      720

Ser  Asn  Arg  Pro  Pro  Ser  Arg  Asn  Ser  Pro  Val  Thr  Ile  Pro  Arg  Ser
               725                      730                      735

Thr  Pro  Ser  His  Arg  Ser  Val  Thr  Pro  Phe  Leu  Gly  Gln  Gln  Gln  Gln
               740                      745                      750

Leu  Gln  Ser  Leu  Val  Pro  Leu  Thr  Pro  Ser  Ala  Leu  Phe  Gly  Gly  Ala
          755                      760                      765

Asn  Phe  Asn  Gln  Ser  Gly  Asn  Ile  Ala  Asp  Ser  Ser  Leu  Ser  Phe  Thr
     770                      775                      780

Phe  Thr  Asn  Ser  Ser  Asn  Gly  Pro  Asn  Leu  Ile  Thr  Thr  Gln  Thr  Asn
785                      790                      795                      800

Ser  Gln  Ala  Leu  Ser  Gln  Pro  Ile  Ala  Ser  Ser  Asn  Val  His  Asp  Asn
               805                      810                      815

Phe  Met  Asn  Asn  Glu  Ile  Thr  Ala  Ser  Lys  Ile  Asp  Asp  Gly  Asn  Asn
               820                      825                      830

Ser  Lys  Pro  Leu  Ser  Pro  Gly  Trp  Thr  Asp  Gln  Thr  Ala  Tyr  Asn  Ala
               835                      840                      845

Phe  Gly  Ile  Thr  Thr  Gly  Met  Phe  Asn  Thr  Thr  Thr  Met  Asp  Asp  Val
     850                      855                      860

Tyr  Asn  Tyr  Leu  Phe  Asp  Asp  Glu  Asp  Thr  Pro  Pro  Asn  Pro  Lys  Lys
865                      870                      875                      880

Glu
```

( 2 ) INFORMATION FOR SEQ ID NO: 2:

( i ) SEQUENCE CHARACTERISTICS:
        ( A ) LENGTH: 236 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO: 2:

```
Met  Ser  Thr  Lys  Lys  Lys  Pro  Leu  Thr  Gln  Glu  Gln  Leu  Glu  Asp  Ala
1              5                        10                       15

Arg  Arg  Leu  Lys  Ala  Ile  Tyr  Glu  Lys  Lys  Lys  Asn  Glu  Leu  Gly  Leu
               20                       25                       30

Ser  Gln  Glu  Ser  Val  Ala  Asp  Lys  Met  Gly  Met  Gly  Gln  Ser  Gly  Val
          35                       40                       45

Gly  Ala  Leu  Phe  Asn  Gly  Ile  Asn  Ala  Leu  Asn  Ala  Tyr  Asn  Ala  Ala
     50                       55                       60

Leu  Leu  Thr  Lys  Ile  Leu  Lys  Val  Ser  Val  Glu  Glu  Phe  Ser  Pro  Ser
65                       70                       75                       80

Ile  Ala  Arg  Glu  Ile  Tyr  Glu  Met  Tyr  Glu  Ala  Val  Ser  Met  Gln  Pro
               85                       90                       95

Ser  Leu  Arg  Ser  Glu  Tyr  Glu  Tyr  Pro  Val  Phe  Ser  His  Val  Gln  Ala
               100                      105                      110

Gly  Met  Phe  Ser  Pro  Lys  Leu  Arg  Thr  Phe  Thr  Lys  Gly  Asp  Ala  Glu
          115                      120                      125

Arg  Trp  Val  Ser  Thr  Thr  Lys  Lys  Ala  Ser  Asp  Ser  Ala  Phe  Trp  Leu
     130                      135                      140

Glu  Val  Glu  Gly  Asn  Ser  Met  Thr  Ala  Pro  Thr  Gly  Ser  Lys  Pro  Ser
145                      150                      155                      160

Phe  Pro  Asp  Gly  Met  Leu  Ile  Leu  Val  Asp  Pro  Glu  Gln  Ala  Val  Glu
               165                      170                      175
```

| | | | | | | | | | | | | |
|---|---|---|---|---|---|---|---|---|---|---|---|---|
|Pro|Gly|Asp|Phe|Cys|Ile|Ala|Arg|Leu|Gly|Gly|Asp|Glu|Phe|Thr|Phe|
| | | |180| | | | |185| | | |190| | | |
|Lys|Lys|Leu|Ile|Arg|Asp|Ser|Gly|Gln|Val|Phe|Leu|Gln|Pro|Leu|Asn|
| | |195| | | | |200| | | |205| | | | |
|Pro|Gln|Tyr|Pro|Met|Ile|Pro|Cys|Asn|Glu|Ser|Cys|Ser|Val|Val|Gly|
| |210| | | | |215| | | |220| | | | | |
|Lys|Val|Ile|Ala|Ser|Gln|Trp|Pro|Glu|Glu|Thr|Phe|
|225| | | |230| | | | | |235| |

( 2 ) INFORMATION FOR SEQ ID NO: 3:

( i ) SEQUENCE CHARACTERISTICS:
        ( A ) LENGTH: 1829 base pairs
        ( B ) TYPE: nucleic acid
        ( C ) STRANDEDNESS: double
        ( D ) TOPOLOGY: linear     ( x i ) SEQUENCE DESCRIPTION: SEQ ID NO: 3:

```
CTAGACATGC TAGTCACCGA GATGTTAGG GAGTACAATC ATAGACATAG CGTGGGGACC    60
ACGCTTGAGG CACTGTTCCA GGGACCACCA GTATACAGAG AGATCAAAAT TAGCGTTGCA   120
CCAGAGACAC CACCACCGCC CGCCATTGCG GACCTGCTCA AATCGGTAGA CAGTGAGGCT   180
GTGAGGGAGT ACTGCAAAGA AAAAGGATGG TTGGTTCCTG AGATCAACTC CACCCTCCAA   240
ATTGAGAAAC ATGTCAGTCG GGCTTTCATT TGCTTACAGG CATTGACCAC ATTTGTGTCA   300
GTGGCTGGAA TCATATATAT AATATATAAG CTCTTTGCGG GTTTTCAAGG TGCTTATACA   360
GGAGTGCCCA ACCAGAAGCC CAGAGTGCCT ACCCTGAGGC AAGCAAAAGT GCAAGGCCCT   420
GCCTTTGAGT TCGCCGTCGC AATGATGAAA AGGAACTCAA GCACGGTGAA AACTGAATAT   480
GGCGAGTTTA CCATGCTGGG CATCTATGAC AGGTGGGCCG TTTTGCCACG CCACGCCAAA   540
CCTGGGCCAA CCATCTTGAT GAATGATCAA GAGGTTGGTG TGCTAGATGC CAAGGAGCTA   600
GTAGACAAGG ACGGCACCAA CTTAGAACTG ACACTACTCA AATTGAACCG GAATGAGAAG   660
TTCAGAGACA TCAGAGGCTT CTTAGCCAAG GAGGAAGTGG AGGTTAATGA GGCAGTGCTA   720
GCAATTAACA CCAGCAAGTT TCCCAACATG TACATTCCAG TAGGACAGGT CACAGAATAC   780
GGCTTCCTAA ACCTAGGTGG CACACCCACC AAGAGAATGC TTATGTACAA CTTCCCCACA   840
AGAGCAGGCC AGTGTGGTGG AGTGCTCATG TCCACCGGCA AGGTACTGGG TATCCATGTT   900
GGTGGAAATG GCCATCAGGG CTTCTCAGCA GCACTCCTCA AACACTACTT CAATGATGAG   960
CAAGGTGAAA TAGAATTTAT TGAGAGCTCA AAGGACGCCG GGTTCCAGT CATCAACACA   1020
CCAAGTAAAA CAAAGTTGGA GCCTAGTGTT TTCCACCAGG TCTTTGAGGG GAACAAAGAA   1080
CCAGCAGTAC TCAGGAGTGG GGATCCACGT CTCAAGGCCA ATTTTGAAGA GGCTATATTT   1140
TCCAAGTATA TAGGAAATGT CAACACACAC GTGGATGAGT ACATGCTGGA AGCAGTGGAC   1200
CACTACGCAG GCCAACTAGC CACCCTAGAT ATCAGCACTG AACCAATGAA ACTGGAGGAC   1260
GCAGTGTACG GTACCGAGGG TCTTGAGGCG CTTGATCTAA CAACGAGTGC CGGTTACCCA   1320
TATGTTGCAC TGGGTATCAA GAAGAGGGAC ATCCTCTCTA AGAAGACTAA GGACCTAACA   1380
AAGTTAAAGG AATGTATGGA CAAGTATGGC CTGAACCTAC CAATGGTGAC TTATGTAAAA   1440
GATGAGCTCA GGTCCATAGA GAAGGTAGCG AAAGGAAAGT CTAGGCTGAT TGAGGCGTCC   1500
AGTTTGAATG ATTCAGTGGC GATGAGACAG ACATTTGGTA ATCTGTACAA AACTTTCCAC   1560
CTAAACCCAG GGGTTGTGAC TGGTAGTGCT GTTGGGTGTG ACCCAGACCT CTTTTGGAGC   1620
AAGATACCAG TGATGTTAGA TGGACATCTC ATAGCATTTG ATTACTCTGG GTACGATGCT   1680
```

| AGCTTAAGCC | CTGTCTGGTT | TGCTTGCCTA | AAAATGTTAC | TTGAGAAGCT | TGGATACACG | 1740 |
| CACAAAGAGA | CAAACTACAT | TGACTACTTG | TGCAACTCCC | ATCACCTGTA | CAGGGATAAA | 1800 |
| CATTACTTTG | TGAGGGGTGG | CATGCCCTC | | | | 1829 |

( 2 ) INFORMATION FOR SEQ ID NO: 4:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO: 4:

GGATCCGGAT CC                12

( 2 ) INFORMATION FOR SEQ ID NO: 5:

( i ) SEQUENCE CHARACTERISTICS:
        ( A ) LENGTH: 2095 base pairs
        ( B ) TYPE: nucleic acid
        ( C ) STRANDEDNESS: double
        ( D ) TOPOLOGY: linear     ( x i ) SEQUENCE DESCRIPTION: SEQ ID NO: 5:

| CGATGGGAAA | AAATTCGGTT | AAGGCCAGGG | GGAAAGAAAA | AATATAAATT | AAAACATATA | 60 |
| GTATGGGCAA | GCAGGGAGCT | AGAACGATTC | GCAGTTAATC | CTGGCCTGTT | AGAAACATCA | 120 |
| GAAGGCTGTA | GACAAATACT | GGGACAGCTA | CAACCATCCC | TTCAGACAGG | ATCAGAAGAA | 180 |
| CTTAGATCAT | TATATAATAC | AGTAGCAACC | CTCTATTGTG | TGCATCAAAG | GATAGAGATA | 240 |
| AAAGACACCA | AGGAAGCTTT | AGACAAGATA | GAGGAAGAGC | AAAACAAAAG | TAAGAAAAA | 300 |
| GCACAGCAAG | CAGCAGCTGA | CACAGGACAC | AGCAGTCAGG | TCAGCCAAAA | TTACCCTATA | 360 |
| GTGCAGAACA | TCCAGGGGCA | AATGGTACAT | CAGGCCATAT | CACCTAGAAC | TTTAAATGCA | 420 |
| TGGGTAAAAG | TAGTAGAAGA | GAAGGCTTTC | AGCCCAGAAG | TAATACCCAT | GTTTCAGCA | 480 |
| TTATCAGAAG | GAGCCACCCC | ACAAGATTTA | AACACCATGC | TAAACACAGT | GGGGGGACAT | 540 |
| CAAGCAGCCA | TGCAAATGTT | AAAAGAGACC | ATCAATGAGG | AAGCTGCAGA | ATGGGATAGA | 600 |
| GTACATCCAG | TGCATGCAGG | GCCTATTGCA | CCAGGCCAGA | TGAGAGAACC | AAGGGGAAGT | 660 |
| GACATAGCAG | GAACTACTAG | TACCCTTCAG | GAACAAATAG | GATGGATGAC | AAATAATCCA | 720 |
| CCTATCCCAG | TAGGAGAAAT | TTATAAAAGA | TGGATAATCC | TGGGATTAAA | TAAAATAGTA | 780 |
| AGAATGTATA | GCCCTACCAG | CATTCTGGAC | ATAAGACAAG | GACCAAAAGA | ACCTTTTAGA | 840 |
| GACTATGTAG | ACCGGTTCTA | TAAAACTCTA | AGAGCCGAGC | AAGCTTCACA | GGAGGTAAAA | 900 |
| ATTGGATGAC | AGAAACCTTG | TTGGTCCAAA | ATGCGAACCC | AGATTGTAAG | ACTATTTTAA | 960 |
| AAGCATTGGG | ACCAGCGGCT | ACACTAGAAG | AAATGATGAC | AGCATGTCAG | GGAGTAGGAG | 1020 |
| GACCCGGCCA | TAAGGCAAGA | GTTTTGGCTG | AAGCAATGAG | CCAAGTAACA | AATACAGCTA | 1080 |
| CCATAATGAT | GCAGAGAGGC | AATTTTAGGA | ACCAAAGAAA | GATGGTTAAG | TGTTTCAATT | 1140 |
| GTGGCAAAGA | AGGGCACACA | GCCAGAAATT | GCAGGGCCCC | TAGGAAAAAG | GGCTGTTGGA | 1200 |
| AATGTGGAAA | GGAAGGACAC | CAAATGAAAG | ATTGTACTGA | GAGACAGGCT | AATTTTTTAG | 1260 |
| GGAAGATCTG | GCCTTCCTAC | AAGGGAAGGC | CAGGGAATTT | TCTTCAGAGC | AGACCAGAGC | 1320 |
| CAACAGCCCC | ACCATTTCTT | CAGAGCAGAC | CAGAGCCAAC | AGCCCCACCA | GAAGAGAGCT | 1380 |
| TCAGGTCTGG | GGTAGAGACA | ACAACTCCCC | CTCAGAAGCA | GGAGCCGATA | GACAAGGAAC | 1440 |
| TGTATCCTTT | AACTTCCCTC | AGATCACTCT | TTGGCAACGA | CCCCTCGTCA | CAATAAAGAT | 1500 |

-continued

| | | | | | | |
|---|---|---|---|---|---|---|
| AGGGGGGCAA | CTAAAGGAAG | CTCTATTAGA | TACAGGAGCA | GATGATACAG | TATTAGAAGA | 1560 |
| AATGAGTTTG | CCAGGAAGAT | GGAAACCAAA | AATGATAGGG | GGAATTGGAG | GTTTTATCAA | 1620 |
| AGTAAGACAG | TATGATCAGA | TACTCATAGA | AATCTGTGGA | CATAAAGCTA | TAGGTACAGT | 1680 |
| ATTAGTAGGA | CCTACACCTG | TCAACATAAT | TGGAAGAAAT | CTGTTGACTC | AGATTGGTTG | 1740 |
| CACTTTAAAT | TTTCCCATTA | GCCCTATTGA | GACTGTACCA | GTAAAATTAA | AGCCAGGAAT | 1800 |
| GGATGGCCCA | AAAGTTAAAC | AATGGCCATT | GACAGAAGAA | AAAATAAAAG | CATTAGTAGA | 1860 |
| AATTTGTACA | GAAATGGAAA | AGGAAGGGAA | AATTTCAAAA | ATTGGGCCTG | AGAATCCATA | 1920 |
| CAATACTCCA | GTATTTGCCA | TAAAGAAAAA | AGACAGTACT | AAATGGAGAA | AATTAGTAGA | 1980 |
| TTTCAGAGAA | CTTAATAAGA | GAACTCAAGA | CTTCTGGGAA | GTTCAATTAG | GAATACCACA | 2040 |
| TCCCGCAGGG | TTAAAAAAGA | AAAAATCAGT | AACAGTACTG | GATGTGGGTG | ATGCA | 2095 |

PROTEASE ASSAYS

This is a division of U.S. application Ser. No. 08/339,901, filed Nov. 3, 1994, now U.S. Pat. No. 5,599,906 which in turn is a file-wrapper continuation under 37 C.F.R. §1.62 of U.S. application Ser. No. 07/923,988, filed Sep. 21, 1992, which is the National Phase of PCT International Application No. PCT/US91/02283, filed Apr. 10, 1991 and designating the Unites States, which PCT Application is in turn a continuation-in-part of U.S. Ser. No. 07/509,007, filed Apr. 13, 1990, now abandoned the benefit of which applications is claimed pursuant to the provisions of 35 U.S.C. §§120, 363 and 365(C).

BACKGROUND OF THE INVENTION

Specific proteolytic enzymes (proteases) play critical roles in a number of important human and animal diseases. In some cases, proteases are essential for the replication of microbial pathogens. In other cases they may have harmful effects on target tissues and organs independent of any microbial involvement.

Among the microbes that depend upon the action of specific proteases are the picornaviruses, which are currently divided into four genera: Enterovirus, Cardiovirus, Rhinovirus and Aphthovirus (foot-and-mouth disease viruses). Coxsackieviruses are picornaviruses within the Enterovirus group which cause a wide spectrum of human diseases, ranging from mild respiratory illness to more serious disseminated diseases of the nervous system and heart (Melnick, J. L., in Virology, 1985, B. N. Fields, Ed., Raven Press, New York, pp. 739–794). Although most of the detailed information on this group of viruses comes from in-depth analyses of poliovirus structure and replication, other members of the picornaviruses have the same genomic organization and appear to function similarly (Rueckert, R. R., in Virology, 1985, B. N. Fields, Ed., Raven Press, New York, pp. 705–738).

The genomes of all picornaviruses comprise a messenger-active single-stranded RNA molecule. This RNA encodes a single large polyprotein that is cleaved to produce both structural and non-structural mature viral proteins. In poliovirus, these cleavages are carried out by two virally-encoded proteases designated 2A and 3C. The 2A protease is responsible for the primary cleavage that generates the viral capsid precursor P1 [Toyoda et al., Cell 45:761 (1986)]. The 3C protease, which is itself released from the polyprotein by an autocatalytic cleavage, then carries out all but one of the remaining cleavage reactions [Hanecak et al., Cell 37:1063 (1984)]. This protease specifically cleaves the peptide bond between certain adjacent glutamine and glycine residues.

Another microbial pathogen dependent upon a specific protease is the human immunodeficiency virus type 1 (HIV-1), the causative agent of most cases of AIDS. The HIV-1 protease, which is part of the pol gene product and is instrumental in the cleavage of large precursor proteins into structural and functional viral proteins, is specific for HIV proteins [Ratner et al., Nature 313:277 (1985); Farmerie et al., Science 236:305 (1987)].

In some cases, proteases are involved in the destructive effects of microbial pathogens in ways that do not involve replicative processes. For example, *Clostridium histolyticum*, a bacterium that causes gas gangrene, secretes a battery of collagenases that produce multiple cleavage of collagen. These collagenases, which specifically cleave at the amino side of glycine residues in peptide linkages, contribute to the invasiveness of the bacterium by destroying the connective-tissue barriers of the host. The bacterium itself is unaffected by its secretory products because it, unlike the multicellular eukaryotes it infects, is devoid of collagen.

Destructive effects of collagenases have also been implicated in disease states which do not involve microbial pathogens. For example, the destruction of connective tissue collagen in bone joints by collagenases in some forms of arthritis is known to occur.

Because the above-mentioned proteases and others are involved in many human and animal diseases, it would be desirable to identify potential inhibitors of the specific proteases involved. Screening assays that can be used to identify such inhibitors, however, are presently laborious to carry out and/or relatively insensitive.

SUMMARY OF THE INVENTION

This invention provides hybrid regulatory proteins comprising a DNA-binding peptide, a linker peptide susceptible to cleavage by a specific protease, and a DNA transcription-modifying peptide; which hybrid proteins are rendered substantially inactive by cleavage of the linker peptide by the protease.

Also provided are DNAs encoding such hybrid proteins, and recombinant vectors comprising such DNAs. These recombinant vectors can be inserted into eukaryotic host cells, thereby forming the basis of relatively rapid and specific assays for proteolytic enzymes of medical and biochemical interest. Eukaryotic cells transformed with such recombinant vectors are also part of this invention.

This invention further provides methods for identifying inhibitors of specific proteases, comprising:
  (a) providing a eukaryotic cell containing:
    (i) a DNA encoding a hybrid regulatory protein comprising a DNA-binding peptide, a linker peptide susceptible to cleavage by a specific protease, and a DNA transcription-modifying peptide, which hybrid regulatory protein is rendered substantially inactive by cleavage of the linker peptide by the protease;
    (ii) a DNA encoding a protease capable of specifically cleaving the linker peptide; and
    (iii) a DNA site responsive to the hybrid regulatory protein, which DNA site is operatively linked to a reporter gene;
  (b) Contacting the eukaryotic cell with a compound suspected to be an inhibitor of the protease; and
  (c) measuring the rate of production of the product of the indicator gene,
whereby an inhibitor of the specific protease is identified by measuring the rate of production of the indicator gene product and comparing such rate to the rate of production of the indicator gene product in the absence of the inhibitor.

BRIEF DESCRIPTION OF THE FIGURE

This invention can be more readily understood by reference to the following detailed description and examples, and to accompanying FIG. 1, which is a schematic representation of the construction of plasmids p1009 and p1013.

DESCRIPTION OF THE INVENTION

All references cited herein are hereby incorporated in their entirety by reference.

As used herein, the term "hybrid regulatory protein" means a protein comprising three peptides (polypeptides)

joined in covalent peptide linkage which together can (a) bind to a specific region of DNA that controls expression of one or more genes or cDNAs and (b) by thus binding alter the rate of transcription of the genes or cDNAs. The alteration in the rate of transcription can be either positive (i.e., the hybrid protein may be a transcription activator) or negative (i.e., the protein may act as a repressor).

Some of the hybrid regulatory proteins of the invention are derivatives of the yeast transcription activator GAL4, a protein of 881 amino acids that is required for galactose catabolism in the yeast *S. cerevisiae*. Ma et al. [Cell 48:847 (1987)] have reported that GAL4 contains two distinct functional domains—a DNA-binding domain containing amino acid residues 1–147 and two activating domains. One activating domain consists of amino acid residues 148–236, the other, residues 768–881. The sequence of amino acid residues 1–881 of GAL4 as disclosed in GenBank is defined in the Sequence Listing by SEQ ID NO: 1. A construct containing the DNA-binding domain and either of the activating domains will function as a DNA transcriptional activator. Therefore, a large in-frame deletion of about the middle third of GAL4 (deleting the first activating domain but retaining the second) does not abolish DNA transcriptional activator activity [Ma et al., Cell 48:847 (1987)].

A fragment of GAL4 consisting of only residues 1–147 retains the ability to bind DNA but cannot activate transcription. The addition of some random acidic peptides containing as few as 15 amino acid residues to the carboxyl terminus of the 1–147 fragment, however, can confer transcription activating activity on the fragment [Giniger et al., Nature 330:670 (1987)].

The GAL4-based hybrid regulatory proteins of the invention comprise:

(a) a DNA-binding peptide having an amino acid sequence corresponding to the sequence of about the first 100 to 150 residues, preferably about the first 147 residues, of the amino terminus of GAL4;

(b) a linker peptide susceptible to cleavage by a specific protease, which linker peptide contains from about 10 to about 250 amino acid residues; and (c) a DNA transcription-activating peptide having an amino acid sequence corresponding to the sequence of about the last 114 residues of the carboxyl terminus of GAL4.

The foregoing three peptides are joined end-to-end in peptide linkage to form the complete hybrid regulatory proteins. The amino acid residue numbers mentioned above relate to the complete amino acid sequence of GAL4 disclosed by Johnston et al. [Proc. Natl. Acad. Sci. USA 79:6971 (1982); Proc. Natl. Acad. Sci. USA 83:6553 (1986)].

Although in an Example below the DNA-binding peptide was to the left of the linker peptide and the transcription-activating peptide was to the right, as viewed from the amino to the carboxyl terminus, the positions of the elements flanking the linker peptide could as well have been reversed. The only requirement for any of the hybrid regulatory proteins of the invention is that the DNA-binding peptide and the transcription-modifying peptide be bridged by the linker peptide.

The linker peptides used in the construction of the hybrid protein can be susceptible to cleavage by specific proteases acting in the cis or trans configuration. Proteases acting in the cis configuration themselves comprise the linker peptide. These proteases are transcribed and translated from the DNAs encoding the hybrid proteins, and they are autoproteolytic. As a result of their activity, the DNA-binding and transcription-activating regions of the hybrid proteins are separated, rendering the cleaved hybrid proteins substantially inactive compared to the intact proteins.

As used herein, the term "substantially inactive" means that a hybrid regulatory protein cleaved by a protease has less than about 20%, preferably less than about 10% and most preferably less than about 5% of the transcription-modifying activity of the uncleaved, intact protein.

When a protease of interest itself serves as the linker peptide, it is desirable to place additional amino acid residues at the amino and/or carboxyl termini of the protease. Such additional residues provide flexibility to permit the protease to assume an active 3-dimensional conformation. These residues can be encoded, e.g., by flanking regions of DNA (a gene or cDNA) encoding the protease. Alternatively, nucleic acid sequences coding for other residues can be engineered in frame into the DNA encoding the protein, using known methods.

Preferably, from about 20 to about 50 or more additional amino acid residues are added to the end(s) of the protease. In an Example below, about 30 additional residues flank both the amino and carboxyl termini of a Coxsackievirus 3C protease linker peptide. In another Example, about 20 to 25 additional residues flank both the carboxyl and amino termini of an HIV-1 protease linker peptide. These additional residues were specified by coding sequences flanking the protease genes, as prepared from viral genetic material.

When a protease that is to be assayed is used in the trans configuration, it is encoded by a second plasmid which is co-transformed with the plasmid encoding the hybrid regulatory protein. In such cases, the linker peptide is not a protease itself but has an amino acid sequence which is recognized and specifically cleaved by the protease.

For example, if the Coxsackievirus 3C protease is used in trans configuration, the linker peptide should contain regions of the viral protein known to be susceptible to cleavage by the protease (Toyoda et al., supra; Hanecak et al., supra). The HIV-1 protease and collagenase require linker peptides having amino acid sequences corresponding to the sequences of their well-known substrates [Meek et al., Proc. Natl. Acad. Sci. USA 86:1841 (1989) (HIV protease); Miller et al., Arch. Biochem. Biophys. 139:104 (1970) (collagenase)]. Trypsin-like proteases specifically cleave at the carboxyl side of lysine and arginine residues. Chymotrypsin-like proteases are specific for cleavage at tyrosine, phenylalanine and tryptophan residues, etc.

The proteases mentioned above are only some of the enzymes that can be assayed by the methods of this invention, and the invention encompasses any protease for which the gene (or cDNA) and substrate specificity are known or determinable.

Preferably, the linker peptide will contain two or more repeats of the susceptible residues, to maximize the probability of cleavage within the linker peptide. Alternatively, the natural substrate of a given protease can be used as the linker peptide. For example, a linker peptide having an amino acid sequence corresponding to that of a collagen molecule can be used, when the protease is a collagenase.

The above-mentioned GAL4-based hybrid regulatory proteins are illustrative of activator-type hybrids that can be made according to the present invention. Other eukaryotic or prokaryotic transcription activators can be modified in analogous fashion. All that is required is that an activator selected have discernible DNA-binding and transcription-activating regions or domains that can be covalently joined by a suitable protease-sensitive linker peptide.

Hybrid transcription repressor proteins are also encompassed by this invention. For example, the phage λ repressor can be modified for use in a protease assay system.

The λ repressor, which is encoded by the cI gene, contains two functional domains. An amino-terminal domain consists of amino acid residues 1–92, using the numbering of the amino acid sequence disclosed by Sauer [Nature 276:301 (1978)]. This domain binds to specific operator (promoter) sites in DNA. A carboxyl-terminal domain consisting of residues 132–236 is instrumental in causing dimerization of the repressor. The sequence of amino acid residues 1–236 of the λ repressor as disclosed in GenBank is defined in the Sequence Listing by SEQ IDNO:2. Dimerization greatly enhances repressor activity. The isolated amino-terminal domain can bind DNA specifically, but it dimerizes very poorly and as a result has an operator affinity that is several orders of magnitude lower, compared to that of the intact protein [Johnson et al., Proc. Natl. Acad. Sci. USA 76:5061 (1979)].

Hybrid regulatory proteins of this invention based upon the λ repressor comprise:

(a) a DNA-binding peptide having an amino acid sequence corresponding to the sequence of about the first 90 to 100 residues, preferably about the first 92 residues, of the amino terminus of the phage λ repressor;

(b) a linker peptide susceptible to cleavage by a specific protease, which linker peptide contains from about 10 to about 250 amino acid residues; and (c) a DNA transcription-modifying peptide having an amino acid sequence corresponding to the sequence of about the last 105 residues of the carboxyl terminus of the phage λ repressor.

The foregoing three peptides are joined end-to-end in peptide linkage to form the complete hybrid regulatory protein. The amino acid residue numbers mentioned above relate to the complete amino acid sequence of the λ repressor disclosed by Sauer, supra.

The linker peptides used in the construction of such hybrid repressor proteins are as described above for hybrid transcription activator proteins. The invention is not limited to λ repressor-based hybrid proteins but also encompasses proteins based upon any repressor comprising (a) a specific DNA binding domain and (b) a second domain, the presence of which is required for the effective functioning of the repressor.

Using published nucleic acid sequence data for a known regulatory protein upon which a hybrid protein of the invention is to be based, and the sequence required to code for the desired linker peptide, DNAs encoding the hybrid regulatory proteins can be chemically synthesized. Such synthesis can be carded out using any of the known methods, such as the phosphoramidite solid support method of Matteucci et al. [J. Am. Chem. Soc. 103:3185 (1981)].

Alternatively, standard recombinant DNA methods can be used to obtain and combine elements needed to construct such DNAs, using genomic or cDNA libraries as sources of the elements. For example, cDNA can be made from messenger RNA (mRNA) isolated from cells known to make the starting regulatory protein, protease and/or protease-susceptible linker peptide, using standard techniques. Such mRNA can be used to produce double-stranded cDNA as described, e.g., by Maniatis et al., supra. This cDNA can be inserted into an appropriate cloning vector which can be used to transform E. coli, to produce a cDNA library.

The cDNA library can be screened using oligonucleotide probes based upon the known nucleotide sequences of DNAs encoding the desired starting regulatory protein, protease and or linker peptide. Such probes can be radiolabeled, e.g., by nick-translation using Pol I DNA polymerase in the presence of the four deoxyribonucleotides, one of which contains $^{32}P$ in the α position (Maniatis et al., supra, page 109). Genomic libraries can be probed in a similar fashion.

Once identified and isolated, the elements needed to construct the hybrid regulatory protein-encoding DNAs of the invention are cleaved by restriction endonucleases as required and inserted into an appropriate eukaryotic cell expression vector.

Many expression vectors known to be useful in eukaryotic cells can be used in this invention. For example, Okayama et al. [Mol. Cell. Biol. 3:280 (1983)] have developed a "pcD" vector system which incorporates Simian virus-40 (SV-40) control elements. Kaufman (U.S. Pat. No. 4,740,461) has described eukaryotic cell vectors which incorporate SV-40 elements and a selectable marker, for co-amplification. Choo et al. [DNA 5:529 (1986)] have developed two recombinant vectors for the direct expression and amplification of cDNA in cultured mammalian cells. Pfarr et al. [DNA 4:461 (1985)] have developed a "modular" vector, pDSP1, which contains two independent mammalian transcription cassettes.

Also useful is a series of mammalian expression vectors which are fully described by Moore et al. in co-pending application Ser. No. 07/486,571, filed Feb. 28, 1990. These vectors are plasmids designated pDSVS, pDSRS, pDSRG, pSRS and pSRG. Plasmid pDSVS contains a β-lactamase gene (conferring ampicillin resistance), a pBR322 origin of replication, a dihydrofolate reductase (DHFR) transcription cassette, an SV-40 promoter, a polylinker containing a number of unique restriction sites, and an SV-40 late region polyadenylation signal sequence.

Plasmid pDSRS is similar to pDSVS except for the substitution of an SRα promoter for the SV-40 promoter of pDSVS. Plasmid pSRS is similar to pDSRS, except that the DHFR transcription cassette has been deleted in pSRS. Plasmids pDSRG and pSRG are similar to pDSRS and pSRS, respectively, except that pDSRG and pSRG contain a human β-globin polyadenylation signal sequence instead of an SV-40 late region polyadenylation signal sequence.

Plasmids pDSVS, pDSRS, pDSRG, pSRS and pSRG were deposited Feb. 21, 1990 with the American Type Culture Collection, Rockville, Md., under the provisions of the Budapest Treaty on the International Recognition of the Deposit of Microorganisms for the Purposes of Patent Procedures. They have been assigned Accession Nos. ATCC 68231, 68232, 68233, 68234 and 68235, respectively. Preferably, a vector selected will be one that can also be cloned in a bacterium such as E. coli, to facilitate recombinant vector construction and replication.

Any vector having control elements operable in yeast cells can also be used in this invention. Methods for preparing useful yeast vectors and strains are well known in the art and have been described, e.g., by Ma et al., Gene 58:201 (1987).

Insertion of the DNA into a cloning and expression vector is easily accomplished when both the DNA and the vector have been cut with the same restriction enzyme(s), since complementary DNA termini are thereby produced. If this cannot be accomplished, it may be necessary to modify the cut ends that are produced by digesting back single-standard DNA to produce blunt ends, or by achieving the same result by filling in the single-stranded termini with an appropriate DNA polymerase. In this way, blunt-end ligation with an enzyme such as T4 DNA ligase may be carried out. Alternatively, any site desired may be produced by ligating oligonucleotides (linkers) onto the DNA termini. Such linkers may comprise specific oligonucleotide sequences that encode restriction site recognition sequences. The cleaved vector and the isolated DNAs may also be modified by homopolymeric tailing, as described by Morrow [Meth. Enzymol. 68:3 (1979)].

Many of the cloning and expression vectors that can be used in this invention contain one or more marker activities that can be used to select for desired transformants, such as ampicillin or tetracycline resistance. Selection of host cells into which such vectors have been inserted is greatly simplified when the host cells otherwise lack the activities contributed by the vectors.

It should be understood that the nucleotide sequences of DNAs inserted at a selected site in a cloning vehicle may include nucleotides that are not part of the actual structural genes. For example, additional nucleotides needed to place the inserted DNAs in frame with translation initiation signals may be present, or linkers may be ligated to the DNAs to adapt them to the cut ends of the vehicle for insertion. As noted above, a DNA sequence encoding a linker peptide which itself is a protease should preferably contain nucleotides encoding additional amino acid residues, so that the protease will be able to achieve an active conformation.

Preferably, DNAs encoding the hybrid regulatory proteins of the invention are under the control of a regulatable promoter, so that expression of the DNAs can be regulated by standard methods until test compounds are introduced into the assay systems. Such methods include, for example, thermal inactivation of a repressor (e.g., the $\lambda$ $P_R$ promoter under the control of the $\lambda$ cI$^{ts}$ gene) and chemical activation or repression (e.g., the lacZ promoter under the control of isopropyl-$\beta$-d-thiogalactopyranoside). In the Examples below, expression of a gene encoding a hybrid transcription activator under the control of the ADHI promoter [Bennetzen et al., J. Biol. Chem. 257:3018 (1982)] was induced by growth in a galactose and glycerol-containing medium.

The recombinant vectors of the invention encoding the hybrid regulatory proteins are used in conjunction with a responsive site that is operatively linked to an indicator gene. DNA bearing a responsive site and linked indicator gene can be introduced into a host cell in a vector. Alternatively, it can be integrated into a chromosome of the cell, using standard methods for stable cell transformation.

As used herein, the term "DNA site responsive to a hybrid regulatory protein" means a DNA site to which the hybrid regulatory proteins specifically bind and thereby modify (either increase or decrease) transcription of an operatively linked indicator gene. In this context, "indicator gene" means a gene or cDNA which encodes an expression product that can readily be measured.

Such a responsive site must of course be compatible with the hybrid regulatory protein used. For the GAL4-based hybrid proteins, for example, a site designated UAS$_G$ (for Upstream Activating Sequence of Galactose) can be used. In the yeast *Saccharomyces cerevisiae*, GAL4 recognizes four sites in UAS$_G$ and, by binding to those sites, upregulates galactose catabolism. Complete UAS$_G$, the nucleotide sequence of which has been disclosed by Guarente et al. [Proc. Natl. Acad. Sci. USA 79:7410 (1982)] and Johnston et al. [Mol. Cell. Biol. 4:1440 (1984)], can be used in yeast cells. Alternatively, a 17 bp element of UAS$_G$ disclosed by Giniger et al. [Cell 40:767 (1985)] and Webster et al. [Cell 52:169 (1988)] can be used. Webster et al. have reported that this 17-mer element mediates GAL4 stimulation almost as efficiently as does UAS$_G$.

Although UAS$_G$ is a natural yeast cis-activating sequence, it or a GAL4-binding element thereof can also be used in mammalian cells. For example, Kakidani et al. [Cell 52:161 (1988)] have reported that a plasmid bearing UAS$_G$ (or a 17-mer element of it) upstream of the start site of the MMTV promoter responded to GAL4 in Chinese hamster ovary (CHO) cells by stimulating transcription of a chloramphenicol acetyltransferase (CAT) gene. UAS$_G$ or an element thereof employed in conjunction with the MMTV promoter in mammalian cells as described by Kakidani et al. can thus be used in this invention.

Lambda repressor-based hybrid regulatory proteins can be used in conjunction with the $P_L$ or $P_R$ promoter [Rosenberg et al., Meth. Enzymol. 101:123 (1983)].

Any of the well-known reporter genes can be operatively linked to one of the foregoing DNA fragments. Examples of suitable reporter genes include but are not limited to *E. coli* $\beta$-galactosidase [An et al., Mol. Cell. Biol. 2:1628 (1982)], xanthine-guanine phosphoribosyl transferase [Chu et al., Nucleic Acids Res. 13:2921 (1985)], galactokinase [Shumperli et al., Proc. Natl. Acad. Sci. USA 79:257 (1982)], interleukin-2 [Cullen, Cell 46:973 (1986)], thymidine kinase [Searle et al., Mol. Cell. Biol. 5:1480 (1985)], firefly luciferase [De Wet et al., Mol. Cell. Biol. 7:725 (1987)], alkaline phosphatase [Henthorn et al., Proc. Natl. Acad. Sci. USA 85:6342 (1988)], secreted placental alkaline phosphatase [Berger et al., Gene 66:1 (1988)] and chloramphenicol acetyltransferase (CAT) [Gorman et al., Mol. Cell. Biol. 2:1044 (1982); Tsang et al., Proc. Natl. Acad. Sci. USA 85:8598 (1988)].

Expression products of the reporter genes can be measured using standard methods. For example, bioassays can be carried out for biologically active proteins such as interleukin-2. Enzyme assays can be performed when the reporter gene product is an enzyme such as alkaline phosphatase. Alternatively, various types of immunoassays such as competitive immunoassays, direct immunoassays and indirect immunoassays may be used.

Such immunoassays involve the formation of immune complexes containing the reporter gene product and and a measurable label. As used herein, the term "label" includes moieties that can be detected directly, such as fluorochromes and radiolabels, and moieties such as enzymes that must be reacted or derivatized to be detected.

In competitive immunoassays, samples from induced cultures (following cell disruption if the reporter gene product is not secreted) are incubated with an antibody against the reporter gene product and a known amount of labeled reporter gene product. Any unlabeled product produced by the cells competes with the labeled material for binding to the antibody. The resulting immune complexes are separated and the amount of labeled complex is determined. The reporter gene product produced by the cells can be quantified by comparing observed measurements to results obtained from standard curves.

Direct immunoassays involve incubating culture samples with a labeled antibody against the reporter gene product and separating any immune complexes that form. The amount of label in the complexes is determined and can be quantified by comparison to standard curves.

Enzyme-linked immunosorbant assays (ELISAs) can also be carried out by well known methods, e.g., as described in U.S. Pat. No. 4,665,018 to Void.

The particular label used will depend upon the type of immunoassay used. Examples of labels that can be used include, e.g., radiolabels such as $^{32}P$, $^{125}I$, $^{3}H$ and $^{14}C$; fluorescent labels such as fluorescein and its derivatives, rhodamine and its derivatives, dansyl and umbelliferone; chemiluminescers such as luciferia and 2,3-dihydrophthalazinediones; and enzymes such as horseradish peroxidase, alkaline phosphatase, lysozyme and glucose-6-phosphate dehydrogenase.

The antibody or reporter gene product, as the case may be, can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels.

Host mammalian cells that have been used to express various recombinant proteins and which can be used in this invention include but are not limited to the African green monkey kidney (COS), Chinese hamster ovary (CHO), NS-1, SP2/0, NIH 3T3, NIH 3T6, C127, CV-1, HeLa, mouse L and Bowes cell lines. Any of the known yeast cell lines can also be used. Cells selected should preferably not normally produce the kind of regulatory protein employed. Alternatively, the cells can be engineered by standard methods to eliminate endogenous synthesis of the protein.

GAL4-based regulatory proteins can be used in unaltered mammalian cells, since GAL4 is a natural yeast transcription activator. Use of GAL4-based hybrid proteins in yeast cells, however, is preferably carried out after prior elimination of endogenous GAL4 production in the cells. This can be accomplished using known methods, such as those described by Ma et al. [Cell 48:847 (1987)] or Rothstein [Meth. Enzymol. 101:202 (1983)]. Such methods result in replacement of the GAL4 gene with a selectable marker such as URA3 or LEU2. In the example below, a yeast strain deleted for both GAL4 and GAL80, a negative regulator of GAL4, was used, although the latter deletion was not necessary for use in this invention.

To carry out the protease assays of the invention, a recombinant plasmid encoding a hybrid regulatory protein is introduced into a host cell containing a responsive site/indicator gene. If the protease to be assayed does not itself comprise the protease-sensitive linker peptide of the protein, a second recombinant plasmid encoding the protease is introduced into the cell. Finally, the cell is contacted with a potential inhibitor of the protease, expression of the regulatory protein is induced, and the rate of production of the indicator gene product is measured.

Inhibition of the protease in an assay employing a repressor-based hybrid regulatory protein will be detected by a decrease in the measured rate of expression of the indicator gene product, compared to the rate in the absence of the inhibitor. The opposite effect will be observed in an activator-based assay. In either case, depending upon the inhibitory power and concentration of the inhibitor, the rate of indicator gene expression will change and will, if inhibition of the protease is complete, reach the level produced by the uncleaved, intact hybrid regulatory protein.

Most compounds tested for protease inhibitory activity will be taken up freely by cultured mammalian cells. The permeability barrier presented by the outer walls of yeast cells can be overcome by standard methods, such as by prior treatment of such cells with lithium acetate as described by Ito et al. [J. Bacteriol. 153:163 (1983)].

To ensure that a compound identified as a specific protease inhibitor by an assay of this invention is not instead merely a general poison to the host cells, it may be desirable to run a control test of the compound in parallel. This is done by exposing control host cells of the same type which harbor an indicator gene not under the control of the hybrid regulatory protein to the compound and measuring the rate of production of this indicator gene product, compared to the rate of production in the absence of the compound. A specific inhibitor of the protease will alter the rate of production of the indicator gene product in the cells in which the indicator gene is under the control of the hybrid protein, but not in the control cells. Such control tests are generally unnecessary, however, when the hybrid regulatory protein is a transcription activator.

EXAMPLES

In the examples that follow, percentages for solids in solid mixtures, liquids in liquids, and solids in liquids are given on a wt/wt, vol/vol and wt/vol basis, respectively, unless otherwise indicated. Sterile conditions were maintained during cell culture.

General Methods

Standard recombinant DNA techniques were carried out essentially as described by Maniatis et al. [Molecular Cloning: A Laboratory Manual, 1982, Cold Spring Harbor Laboratory]. The restriction enzymes, DNA polymerase I (Klenow fragment) and DNA ligase used were products of New England Biolabs, Beverly, Mass., and the conditions for the use of these enzymes were essentially those of the manufacturer.

Cell Cultures

E. coli strain XL1-Blue (Stratagene Inc., La Jolla, Calif.) was used for cloning all plasmid constructs. The bacteria were grown at 37° C. in LB broth (Maniatis et al., supra page 68) containing 100 µg/ml ampicillin.

Yeast strain GGY1::171 (ΔGAL4, ΔGAL80, Ura3, His 3 and Leu 2) carries a GAL1-lacZ fusion gene activated by GAL4 at the $UAS_G$ site and does not produce its own GAL4. Stimulation of this and similar strains by exogenous GAL4 produces a readily measured increase in β-galactosidase activity.

The yeast cells were grown in YEPD medium [1% yeast extract (DIFCO Laboratories, Detroit, Mich.), 2% Bacto Peptone (Difco), 0.004% adenine sulfate (Sigma Chemical Co., St. Louis, Mo.) and 2% dextrose (Sigma); Sherman et at., Methods in Yeast Genetics, 1983, Cold Spring Harbor Laboratory, Cold Spring Harbor, N.Y.] at 30° C. to log phase ($5 \times 10^6$ to $10^7$ cells/ml). Growth was followed by measuring $OD_{600}$ in a conventional spectrophotometer, with 1 $OD_{600}$ unit equivalent to about $10^7$ cells per ml.

To induce cells harboring plasmids of the invention for β-galactosidase assay, the cells were washed and then cultured at 30° C. in YEPGal-Gly medium containing 1% yeast extract, 2% peptone, 0.004% adenine sulfate, 2% galactose and 2% glycerol. Incubation in this medium (induction medium) was carried out for about 20 hours prior to assay.

β-Galactosidase Assays

X-gal indicator plates were prepared as described by Osley et al. [Proc. Natl. Acad. Sci. USA 79:7689 (1982)]. Assay in X-gal (5-bromo-4-chloro-3-indolyl-β-D-galactoside) plates was carried out by observing the ability of cell colonies synthesizing β-galactosidase to produce blue colored spots on the plates.

Liquid β-galactosidase assays were performed by aliquoting 50 µl of yeast cells in induction medium into 96-well microtiter plates (Falcon) at a concentration of $1 \times 10^6$ cells/ ml. Additional induction medium containing lithium acetate was added to each well to give a final lithium acetate concentration of 10 mM and a final volume of 250 μl. Inclusion of the lithium acetate in the medium facilitated the uptake of small molecules by the yeast cells. The plates were incubated at 30° C. for about 20 hours, after which the cells were pelleted by centrifuging the plate at 4,000×g for 30 minutes, and the supernatant fluid was removed from each well by gentle aspiration.

β-galactosidase activity was measured by adding 100 μl of freshly-prepared MUG Reagent [Geballe et al., Cell 46:865 (1986); Mallon et al., J. Virol. 64:6282 (1990)] mixture [4:1 (vol:vol) MUG Reagent (12.5 mg 4-methylumbelliferyl β-D-galactoside in 100 ml distilled water): buffer (0.6 M $Na_2HPO_4$, 0.4M $NaH_2PO_4$, 0.01M KCl, 0.001M $MgSO_4$, 2.7 ml/liter β-mercaptoethanol)] to each well. The plates were incubated at 37° C. for one to two hours and then read on a Dynatech (Chantilly, Va.) Microfluor plate reader with the excitation and emission wavelengths set at 365 and 450 nm, respectively.

Cell Transformation

*E. coli* strain XL1-Blue was transformed using $CaCl_2$ as described by Maniatis et al., supra page 250. Transformants were selected on plates containing 100 μg/ml ampicillin.

Yeast strain GGY1::171 was transformed using lithium acetate as described by Ito et al., supra. Plasmids were introduced and selected on appropriate dropout plates (Sherman et al., supra).

Coxsackievirus 3C Protease Assay

Construction of Plasmids p1009 and p1013

Figure 1:
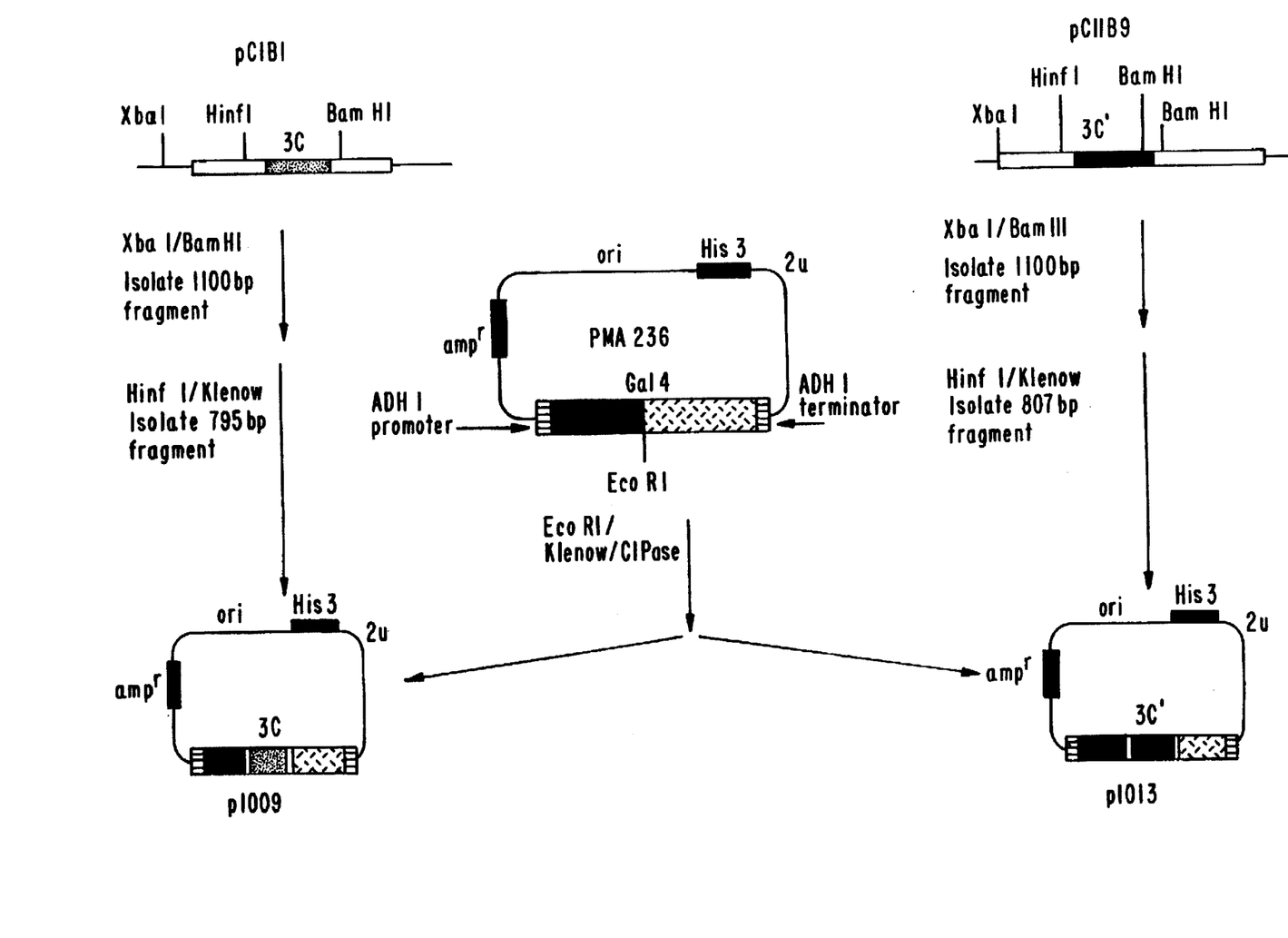

Construction of both plasmids entailed modification of plasmid pMA236 [Cell 48:847 (1987)]. This plasmid contains a truncated GAL4 gene in which nucleotides encoding residues 1–147 of the DNA-binding domain and residues 768–881 of the transcription-activating domain of GAL4 are joined by a unique EcoRI restriction site. Plasmid pMA236 was modified by cleavage at the EcoRI site and insertion of a functional (p1009) or non-functional (p1013) Coxsackievirus 3C protease at the cleavage site. Both constructions are shown schematically in FIG. 1.

In preparation for making plasmid p1009, plasmid $pCB111_{35}$ [Tracy et al., Arch. Virol. 85:157 (1985)] was digested with PstI and AvaI, and a fragment containing the CVB3 sequence (including the 3C coding region) was ligated into the PstI and AvaI sites of transcription plasmid pGEM2 (Promega Corp., Madison, Wis.). The resulting plasmid pB1C13 was digested with XbaI and treated with the Klenow fragment of DNA polymerase I to fill in the 5' protruding ends. A large fragment (about 4.5 kb) isolated after PstI digestion of pB1C13 was ligated to a DNA fragment containing the 5' end sequences of BBV RNA1, to make plasmid pC1B1. This plasmid contains nucleotides corresponding to bases 4947 to 6775 of the CVB3 gene sequence [Lindberg et al., Virology 156:50 (1987)]. The sequence of bases 4947–6775 of the CVB3 gene is defined in the Sequence listing by SEQ ID NO: 3, wherein base 1 corresponds to base 4947 of the complete sequence as disclosed in GenBank. The DNA fragment from BBV RNA1 had been obtained by BanI cleavage of plasmid p1B9SP [Dasmahapatra et al., Proc. Natl. Acad. Sci. USA 83:63 (1986)], isolation of a 310 bp fragment, HinfI/Klenow treatment of the fragment, PstI digestion and isolation of a 48 bp fragment.

Plasmid p1009 was constructed by cleaving pC1B1 with XbaI and BamHI and isolating an 1100 bp fragment encoding wild-type Coxsackievirus 3C protease. The isolated fragment was further digested with HinfI and treated with Klenow fragment to fill in the cut ends. A 795 bp DNA fragment was then isolated and ligated to plasmid pMA236 which had been cleaved with EcoRI, treated with calf intestinal phosphatase to remove 5' phosphate groups and end-filled with Klenow fragment. Plasmid p1009 contains nucleotides corresponding to bases 5254 to 6052 of the CVB3 gene sequence.

In preparation for the construction of p1013, plasmid pC11B9 was made by inserting a 12 bp linker (GGATCCGGATCC) SEQ ID NO: 4 at the BalI site of plasmid pC1B1. This in-frame insertion, which encoded an additional four amino acid residues on the carboxyl side of residue 166 of the wild-type Coxsackievirus 3C protease, produced a protein that was proteolytically inactive in both the cis and trans configurations.

Plasmid p1013 was constructed by cleaving pC11B9 with XbaI and BamHI, and isolating an 1100 bp fragment. This fragment was digested with HinfI and blunt ended with Klenow fragment, and an 807 bp fragment was isolated. This isolated fragment was ligated to pMA236 which had been linearized with EcoRI, dephosphorylated and Klenow blunt ended.

Both plasmid p1009 and p1013 were characterized by restriction enzyme analysis and by nucleotide sequencing [primer extension method; Sanger et al., Proc. Natl. Acad. Sci. USA 74:5463 (1977)] at the junction of the yeast and viral sequences.

Effect of Plasmids p1009 And p1013 On β-Galactosidase Activity In Yeast Cultures To demonstrate the use of plasmid p1009 as part of a potential screening assay for inhibitors of Coxsackievirus 3C protease, plasmids p1009 and p1013 were transformed into yeast strain GGY1::171. The transformants were then streaked onto an X-gal plate, cultured and induced with galactose and glycerol as described above. Transformants containing plasmid pMA210 were also prepared and cultured on the plate, together with untransformed strain GGY1::171 and the p1009 and p1013 transformants. Plasmid pMA210 [Ma, Cell 48:847 (1987)] encodes the full wild-type GAL4 protein.

Yeast cells harboring plasmids p1013 and pMA210 produced appreciable amounts of β-galactosidase activity, as evidenced by visible blue spots on the plate at the positions of the cells. Both of these cells produced intact transcription activators which bound to the $UAS_G$ site, thereby turning on expression of the β-galactosidase genes operatively linked to that site.

In contrast, untransformed yeast cells showed essentially no β-galactosidase activity (essentially no color reaction), as did cells harboring plasmid p1009. The latter cells produced a hybrid regulatory protein which, due to the presence of the functional 3C protease between the DNA-binding and transcription-activating domains, underwent autoproteolysis. As a consequence, an intact transcription activator was not available in these cells to stimulate β-galactosidase production at the $UAS_G$ site.

Similar results were obtained in a quantitative liquid β-galactosidase assay carried out as described above. These results are shown in Table 1.

TABLE 1

| Cocksackievirus 3C Protease Assay | |
|---|---|
| Plasmid | β-Galactosidase Activity* |
| None | — |
| pMA236 | 3,877 |
| p1013 | 433 |
| p1009 | 14 |

*β-Galactosidase activity in MUG units was obtained by subtracting fluorescence values obtained with the MUG reagent mixture only from all values measured.

Had a specific inhibitor of the 3C protease been present in the cells containing plasmid p1009, autoproteolysis would have been prevented, the hybrid regulatory protein would have remained intact, and the result would have been markedly increased β-galactosidase activity in both assays.

HIV-1 Protease Assay

Construction of Plasmids pHP236 and pHP236m

By analogy to the construction of plasmid p1009, a plasmid designated pHP236 was constructed by inserting a DNA encoding an HIV-1 protease-linked hybrid regulatory protein into plasmid pMA236. Like plasmid p1009, the resulting construct contained nucleotides encoding residues 1–147 of the DNA-binding domain and residues 768–881 of the transcription-activating domain of GAL4. These GAL4 elements were separated in pHP236, however, by an HIV-1 protease peptide linker.

To construct plasmid pHP236, a plasmid designated pBD1091 was first constructed by digesting λHXB-2 [a subclone of HIV-1 genomic DNA; Shaw et al., Science 226:1165 (1984)] with ClaI, filling the 5' overhangs with the Klenow fragment of E. coli DNA polymerase and partially digesting with NsiI. A 2,095 bp ClaI-NsiI fragment was purified and cloned into plasmid PKK233-2 (Pharmacia LKB Biotechnology, Piscataway, N.J.) which had been linearized with NcoI, blunt-ended with Klenow polymerase and digested with PstI. Plasmid pBD1091 contains DNA having the nucleotide sequence of nucleotides 829–2924 of HIV-1 [Starcich et al., Science 227:538 (1985); Ratner et al., Nature 313:277 (1985)] under the control of the λtrc promoter. The sequence of bases 829–2923 of HIV-1 is defined in the Sequence Listing by SEQ ID NO: 5, wherein base 1 corresponds to base 829 of the complete sequence as disclosed in GenBank. These nucleotides encode part of gag, all of the protease and part of the reverse transcriptase of HIV-1 in a single reading frame.

Plasmid pBD1091 was cleaved with BgIII, blunt ended with Klenow polymerase and ligated to produce plasmid pBD1140, which contained a newly-created ClaI restriction endonuclease site in the HIV-1 sequence. Plasmid pBD1140 was digested with PvuII and BalI, and a 1,509 bp DNA fragment containing the HIV-1 nucleotide sequence from nucleotides 1145–2654 was subcloned into the EcoRV site of plasmid pSP71 (Promega Corporation, Madison, Wis.).

The resulting plasmid, designated pHP71, was digested with ClaI and treated with Klenow polymerase to produce a 568 bp DNA fragment containing nucleotides 2093–2654 of HIV-1 (the protease of HIV-1 is encoded by nucleotides 2286–2582) and 7 nucleotides from the vector DNA. This fragment was isolated and cloned into plasmid pMA236, which had been linearized with EcoRI, treated with calf intestinal alkaline phosphatase and blunt ended with Klenow polymerase, to produce plasmid pHP236.

Plasmid pHP236m, an analog of plasmid pHP236 encoding a mutant, inactive HIV-1 protease linking the two functional domains of GAL4, was constructed by digesting plasmid pART2 m118 [Loeb et al., J. Virol. 63:111 (1989)] with BgIII and BalI. A 560 bp fragment was isolated, treated with Klenow polymerase and subcloned into pSP71 which had been digested with ClaI and HindIII and blunt-ended with Klenow polymerase. The resulting plasmid, pHP71m, was digested with EcoRV and XhoI, and a 583 bp DNA fragment encoding the mutant protease was isolated. The ends of the fragment were filled with Klenow polymerase, and the fragment was cloned into plasmid pMA236 which had been cleaved with EcoRI and blunt ended with Klenow polymerase. Both plasmid pHP236 and pHP236m were characterized as described above.

Effect of Plasmids pHP236 And pHP236m On β-Galactosidase Activity In Yeast Cultures To demonstrate the use of plasmid pHP236 as part of a potential screening assay for inhibitors of the HIV-1 protease, plasmids pHP236 and pHP236m were transformed into yeast strain GGY1::171. The transformants were then streaked onto an X-gal plate, cultured and induced with galactose and glycerol as described above. Untransformed strain GGY1::171 was also cultured on the plate together with the pHP236 and pHP236m transformants.

Yeast cells harboring plasmids pHP236m produced appreciable amounts of β-galactosidase activity, as evidenced by a visible blue spot on the plate at the position of the cells. Since the protease encoded by plasmid pHP236m was inactive and incapable of cleaving the linker peptide, these cells produced an intact transcription activator which bound to the $UAS_G$ site, thereby turning on expression of the β-galactosidase genes operatively linked to that site.

In contrast, untransformed yeast cells showed essentially no β-galactosidase activity (essentially no color reaction), as did cells harboring plasmid pHP236. The latter cells produced a hybrid regulatory protein which, due to the presence of the functional HIV-1 protease between the DNA-binding and transcription-activating domains, underwent autoproteolysis. As a consequence, an intact transcription activator was not available in these cells to stimulate β-galactosidase production at the $UAS_G$ site.

Similar results were obtained in a quantitative liquid β-galactosidase assay carried out as described above, as shown in Table 2.

TABLE 2

| HIV-1 Protease Assay | |
|---|---|
| Plasmid | β-Galactosidase Activity* |
| None | — |
| pHP236 | 68 |
| pHP236m | 3,178 |

*β-Galactosidase activity in MUG units was obtained by subtracting fluorescence values obtained with the MUG reagent mixture only from all values measured.

Had a specific inhibitor of the HIV-1 protease been present in the cells containing plasmid pHP236, autoproteolysis would have been prevented, the hybrid regulatory protein would have remained intact, and the result would have been markedly increased β-galactosidase activity in both assays.

Plasmid Deposits

E. coli strain XLI Blue harboring plasmid p1009 was deposited Mar. 29, 1990 with the American Type Culture Collection (ATCC), Rockville, Md., and assigned Accession No. ATCC 68282. The same bacterial strain harboring plasmid pHP236 was deposited Mar. 13, 1991 with the ATCC and assigned Accession No. ATCC 68563. Both deposits were made under the provisions of the Budapest Treaty on the International Recognition of the Deposit of Microorganisms for the Purposes of Patent Procedures.

Many modifications and variations of this invention may be made without departing from its spirit and scope, as will become apparent to those skilled in the art. The specific embodiments described herein are offered by way of example only, and the invention is to be limited only by the terms of the appended claims.

What is claimed is:

1. A DNA encoding a hybrid regulatory protein comprising a DNA-binding peptide, a linker peptide, and a DNA transcription-modifying peptide, wherein the linker peptide bridges the DNA-binding peptide and the transcription-modifying peptide and is susceptible to cleavage by a specific protease that (a) is essential for replication of microbial pathogens or causes harmful effects on target tissues and organs; and (b) is not capable of cleaving the protein(s) from which the DNA-binding and transcription-modifying peptides are derived; which hybrid regulatory protein is (a) capable of binding to a specific region of DNA that controls the expression of one or more genes, thereby altering the rate of expression of the genes, and is (b) rendered substantially inactive by cleavage of the linker peptide by the protease, wherein substantially inactive means that the cleaved protein has 20% or less of the transcription-activating activity of the uncleaved, intact protein.

2. A recombinant vector comprising a DNA encoding a hybrid regulatory protein comprising a DNA-binding peptide, a linker peptide, and a DNA transcription-modifying peptide, wherein the linker peptide bridges the DNA-binding peptide and the transcription-modifying peptide and is susceptible to cleavage by a specific protease that (a) is essential for replication of microbial pathogens or causes harmful effects on target tissues and organs; and (b) is not capable of cleaving the protein(s) from which the DNA-binding and transcription-modifying peptides are derived; which hybrid regulatory protein is (a) capable of binding to a specific region of DNA that controls the expression of one or more genes, thereby altering the rate of expression of the genes, and is (b) rendered substantially inactive by cleavage of the linker peptide by the protease, wherein substantially inactive means that the cleaved protein has 20% or less of the transcription-activating activity of the uncleaved, intact protein; which recombinant vector has regulatory elements that permit the DNA to be transcribed in a eukaryotic cell.

3. The recombinant vector of claim 2 in which the DNA encodes a hybrid regulatory protein that is a repressor of DNA transcription.

4. The recombinant vector of claim 2 in which the DNA encodes a hybrid regulatory protein that is an activator of DNA transcription.

5. The recombinant vector of claim 2 in which the DNA encodes a hybrid regulatory protein wherein the linker peptide is susceptible to cleavage by Coxsackievirus 3C protease or HIV-1 protease.

6. The recombinant vector of claim 4 in which the DNA encodes a hybrid regulatory protein wherein the amino acid sequences of the DNA-binding peptide and the DNA transcription-modifying peptide correspond to amino acid sequences of GAL4.

7. The recombinant vector of claim 2 which is plasmid p1009 or pHP236, which plasmids have been deposited with the American Type Culture Collection and assigned Accession Nos. ATCC 68282 and ATCC 68,563, respectively.

8. A eukaryotic cell comprising:

(a) a DNA encoding a hybrid regulatory protein comprising a DNA-binding peptide, a linker peptide, and a DNA transcription-modifying peptide, wherein the linker peptide bridges the DNA-binding peptide and the transcription-modifying peptide and is susceptible to cleavage by a specific protease that (i) is essential for replication of microbial pathogens or causes harmful effects on target tissues and organs; and (ii) is not capable of cleaving the protein(s) from which the DNA-binding and transcription-modifying peptides are derived; which hybrid regulatory protein is (i) capable of binding to a specific region of DNA that controls the expression of one or more genes, thereby altering the rate of expression of the genes, and is (ii) rendered substantially inactive by cleavage of the linker peptide by the protease, wherein substantially inactive means that the cleaved protein has 20% or less of the transcription-activating activity of the uncleaved, intact protein;

(b) a DNA encoding a protease capable of specifically cleaving the linker peptide; and (c) a DNA site responsive to the uncleaved hybrid regulatory protein, which DNA site is operatively linked to a reporter gene.

9. The recombinant vector of claim 2 in which the DNA is under the control of a regulatable promoter.

10. The recombinant vector of claim 6 in which the DNA encodes a hybrid protein wherein the amino acid sequences of the DNA-binding peptide and the DNA transcription-modifying peptide are the amino acid sequences of residues 1–147 and 768–881, respectively, of GAL4, as set forth in SEQ ID NO: 1.

11. The recombinant vector of claim 10 in which the hybrid gene encodes a hybrid protein wherein the linker peptide is susceptible of cleavage by Coxsackievirus 3C protease, HIV-1 protease or collagenase.

12. The recombinant vector of claim 1 in which the hybrid gene encodes a hybrid protein wherein the linker peptide is Coxsackievirus 3C protease.

13. The recombinant vector of claim 3 in which the DNA encodes a hybrid protein wherein the amino acid sequences of the DNA-binding peptide and the DNA transcription-modifying peptide correspond to amino acid sequences of the λ phage repressor.

14. The eukaryotic cell of claim 8 in which the DNA is under the control of a regulatable promoter.

15. The eukaryotic cell of claim 14 in which the hybrid protein is a repressor of DNA transcription.

16. The eukaryotic cell of claim 14 in which the hybrid protein is an activator of DNA transcription.

17. The eukaryotic cell of claim 16 in which the DNA encodes a hybrid protein wherein the amino acid sequences of the DNA-binding peptide and the DNA transcription-modifying peptide correspond to amino acid sequences of GAL4.

18. The eukaryotic cell of claim 17 in which the DNA encodes a hybrid protein wherein the amino acid sequences of the DNA-binding peptide and the DNA transcription-modifying peptide are the amino acid sequences of residues 1—147 and 768–881, respectively, of GAL4, as set forth in SEQ ID NO: 1.

19. The eukaryotic cell of claim 18 in which the DNA encodes a hybrid protein wherein the linker peptide is susceptible to cleavage by Coxsackievirus 3C protease, HIV-1 protease or collagenase.

20. The eukaryotic cell of claim 19 in which the DNA encodes a hybrid protein wherein the linker peptide is susceptible to cleavage by Coxsackievirus 3C protease.

21. The eukaryotic cell of claim 20 which harbors plasmid p1009.

22. The eukaryotic cell of claim 19 in which the DNA encodes a hybrid protein wherein the linker peptide is susceptible to cleavage by HIV-1 protease.

23. The eukaryotic cell of claim 20 which harbors plasmid pHP236.

24. The eukaryotic cell of claim 8 which is a mammalian cell or a yeast cell.

25. The eukaryotic cell of claim 8 in which the measurable product is β-galactosidase.

* * * * *